United States Patent [19]

Amend

[11] 4,287,179
[45] Sep. 1, 1981

[54] IMMERSION VACCINE FOR ENTERIC REDMOUTH

[75] Inventor: Donald F. Amend, Lynnwood, Wash.

[73] Assignee: Tavolek Inc., Redmond, Wash.

[21] Appl. No.: 111,142

[22] Filed: Jan. 10, 1980

Related U.S. Application Data

[63] Continuation-in-part of Ser. No. 938,604, Aug. 31, 1978, abandoned.

[51] Int. Cl.³ .............................................. A61K 39/02
[52] U.S. Cl. ....................................................... 424/92
[58] Field of Search ........................................... 424/92

[56] References Cited

U.S. PATENT DOCUMENTS 4,009,259  2/1977  Ament et al. ........................... 424/89

OTHER PUBLICATIONS

Amend et al., Science 192 (4241): 793–794 May 21, 1976 Uptake of Bovine Serum Albumin by Rainbow Trout from Hyperosmotic Solutions: A Model for Vaccinating Fish.

Antipa et al., (1977) Canada J. Fish. Res. Bd. 34 (2): 203–208 Immunization of Pacific Salmon Comparison of Injection and Hyperosmotic Infiltration of *Vibrio anguillarum* and *Aeromonae salmonicida* Bacterins.

Amend (1976) Canada J. Fish. Res. Bd. 33 (4): 1059–1066 Prevention and Control of Viral Diseases of Salmonids.

N.T.I.S. Pb–211 833 25 Mar. 1977 Hyperosmotic Infiltration of Bioaffecting Agents into Fish Dept. Interior Wash. D. C. 16 pp. (Filmed 11.3.77).

N.T.I.S. Pb 279–576 Dec. 1977 Fryer et al. Development of Bacterins and Vaccines for Control of Infectious Diseases in Fish 10 pp.

Ewing et al. Int. J. Sys. Bact. 28 (1):37–44 Jan. 1978 *Yersinia ruckeri* Sp. Nov., The Redmouth (RM) Bacterium.

Fender et al., Canada Fish Res. Bd. J. 35 (6): 871–874 (1978) Hyperosmotic Infiltration: Factors Influencing Uptake of Bovine Serum Albumin by Rainbow Trout (*Salmo gairdneri*).

"Description of a Bacterium Associated With Redmouth Disease of Rainbow Trout (*Salmo gairdneri*)'-'–Canadian Journal of Microbiology vol. 12, 1966, pp. 763–770.

*Primary Examiner*—Shep K. Rose

[57] ABSTRACT

The invention involves the immunizing of fish against Enteric Redmouth by immersing the fish in a vaccine prepared from killed organisms of *Y. ruckeri*.

4 Claims, No Drawings

IMMERSION VACCINE FOR ENTERIC REDMOUTH

This is a continuation-in-part to Application Ser. No. 938,604 filed Aug. 31, 1978, now abandoned.

TECHNICAL FIELD

This invention relates to a vaccine for protection against Enteric Redmouth. The vaccine is obtained from *Yersinia ruckeri*. The vaccination of fish with the vaccine is accomplished by a simple immersion technique.

BACKGROUND OF THE INVENTION

Enteric Redmouth, a bacterial disease of salmonid trout, can be a serious problem with intensively cultured species of fish and is one of the limiting factors in the culture of trout. The disease can occur at any time of the year, especially when water temperatures exceed 14° C. Consequently, it is most prevalent in the warmer summer months. Outbreaks can be expected when the water temperatures reach 14°–20° C.

Enteric Redmouth is caused by the organism, *Yersinia ruckeri*. This bacterium is a gram-negative, motile rod, approximately 1×3 nm. The motile organisms can frequently be seen in wet slides of fresh kidney or spleen smears from infected fish (900×magnification). It is prevalent throughout North America, primarily in the major trout producing areas.

Vaccination against Enteric Redmouth is gaining popularity among aquaculturists as a prophylactic control method. However, the lack of a convenient efficacious delivery method applicable to mass immunization of fish has limited the use of vaccines for controlling Enteric Redmouth. Although several techniques are available for mass inoculation, for example, oral delivery, injection and forced fluid influx procedures such as vacuum infiltration, hyperosmotic infiltration and pressurized (generally about 90–100 p.s.i.) spray vaccination, each method, except injection, delivers unquantitative vaccine doses.

For example, incorporation of vaccine bacterins into the diet is a desirable delivery system because of its ease of administration. However, the degree and duration of immunity conferred is generally less than delivery by injection. This is perhaps due to the difficulty of ensuring uniform dosage uptake of the diet by the fish.

With regard to the injection technique, the inherent disadvantage is obvious. Although fish can be injected individually on a limited scale, the individual injection of millions of small fish is not practical.

The disadvantages of pressurized spray vaccination techniques are its inapplicability to small fish weighing less than four grams and the possible hypersensitization to the vaccine by the user due to the inherent aerosol mist produced by the technique. Forced fluid influx procedures such as vacuum infiltration and hyperosmotic infiltration possess a serious disadvantage in the traumatic physiological response of fish to the stress induced by these pressurized procedures. In addition, hyperosmotic infiltration procedures may require the additional step of pretreatment in a hyperosmotic solution of, for instance, urea, or NaCl, before hyperosmotic exposure to the vaccine solution.

Whereas, it had previously been thought that a pressurized procedure was necessary to affect vaccine absorption by fish, it has now been found that the mass inoculation of salmon and trout against Enteric Redmouth can be readily accomplished without the aforementioned disadvantages by simple non-pressurized immersion in a vaccine derived from *Y. ruckeri*.

DESCRIPTION OF THE INVENTION

An object of this invention is to provide a vaccine solution useful in immunizing marine fish against Enteric Redmouth wherein the immunogenic agent is inactivated *Y. ruckeri*.

Another object of this invention is to provide a method of immunizing fish by simple non-pressurized immersion in the aforementioned vaccine solution.

The main causitive agent found to be associated with Enteric Redmouth is *Y. ruckeri*, although another less frequently encountered strain is known to exist [e.g., see R. A. Busch, Marine Fisheries Review. 40,42 (1978) and P. O'Leary, Masters Thesis, Oregon State University (1977)]. When the live virulent form of this agent is administered to salmonids, the clinical symptoms of the disease including death are exhibited. The administration of this live virulent agent can thus be used as a method of challenging a potential vaccine to test its immunogenic properties against same. The vaccine of this invention has accordingly been found to be effective in immunizing susceptible fish when challenged with infectious doses of the agent. It is thus contemplated that the vaccine of this invention may be used to significantly control the incidence of Enteric Redmouth in fish.

The virulent bacterial agent, (Strain 126-76) used in making the vaccine described hereinafter was obtained from Dr. R. A. Busch, Rangen Research Laboratory, Rt. 1, Hagerman, Idaho 83332.

The Hagerman strain of *Y. ruckeri* was isolated from rainbow trout (*Salmo gairdneri*) November 1976 at the Rangen Research Laboratory, Hagerman, Idaho. The isolate used herein was obtained from the Rangen Research Laboratory on June 23, 1977. This is a typical Enteric bacterium; gram-negative, motile, oxidase negative, anaerogenic fermenter, and methyl red positive, indole production negative.

Biochemical and serological description of the organism is reported by A. J. Ross et al., Canadian J. Microbiology 12 (1966) in Table 1 on Page 766.

In general, the invention herein requires that following the growth of *Y. ruckeri* cells in a proper liquid nutritive medium, a vaccine be prepared by killing the cells, preferably by chemical inactivation means. Prior to inactivation, the potency can be enhanced by briefly raising the pH to 9.8 then lowered to pH 7.0.

Cells of *Y. ruckeri* can be grown in any suitable sterile liquid medium supplying all metabolic requirements such as tryptic soy broth (see Example 5), also known as soybean casein digest. Preferred temperatures for growth are 20° to 28° C. and for maximum yield the culture should be aerated during growth. The pH must be maintained between 7.0 and 7.2 and the culture harvested between 40 and 72 hours.

As presented herein, a disclosure of a preferred embodiment of the invention appears with reference to development of a vaccine from the aforementioned isolate of *Y. ruckeri*. The invention, however, is not to be deemed limited to said particular isolate.

Injection of the aforementioned isolate into susceptible rainbow trout, maintained at 15° C., confirmed virulency. The virulent organism was then reisolated by culturing an infected kidney sample from the moribund fish, obtained by inserting a sterile needle into the fish kidney, on tryptic soy agar (see Example 6), also known as soybean casein digest, at 20° C. for 24 hours. Colonies were checked for purity and typical serological and biochemical reactions confirmed to thereby provide a pure subculture on tryptic soy agar. A "master seed" was obtained by then growing the organism in mist desiccans (see Example 7) at 20° C. for 24 hours followed by lyophilization in 2 ml ampules thereafter stored at −70° C.

A "working seed" was prepared by aseptically adding 0.5 ml of tryptic soy broth (see Example 5) to an ampule of lyophilized master seed. The contents of the rehydrated seed culture were then added to a 3-liter flask containing 1500 ml of tryptic soy broth. The working seed was incubated with agitation at 22° C. for 24 hours to provide sufficient growth of the virulent organism. Growth is measured by monitoring turbidity. After 40 hours incubation, an optical density of at least 0.8 using a 13 mm tube in a spectrophotometer (Spectronic 20 by Bausch and Lomb) at 525 nm was reached.

The foregoing 1500 ml working seed provided the inoculum for the respective production culture: the 1500 ml was added to 1200 liters to tryptic soy broth in an 1800-liter stainless steel production fermenter. The production culture was incubated at 22° C. for 48 hours with constant agitation and aeration using sterile air through a sparge unit at a rate of 0.25 cu. ft./min. The pH of the production culture was maintained between 7.0 and 7.2 by the addition of 10 N sodium hydroxide. Prior to inactivation of the live, virulent organism, the culture was examined for purity by the conventional procedures of gram staining, culturing and serological reaction to specific antisera. The pH is then increased to 9.8 by addition of 10 N NaOH. After 30 minutes, the pH is lowered to pH 7.0 to 7.4 by addition of 10 N HCl.

The production culture was then chemically inactivated by adding 0.3% (vol/vol) formalin followed by incubation at 4° C. for 48 hours. The inactivated bacterial preparation constituted the bacterin material for the vaccine. The bacterin was tested for sterility prior to use, for example, by the standard procedure of incubating tryptic soy broth and thioglycolate broth for 14 days at 22° and 37° C. to observe organism growth. Finally, to each bacterin was added 1.2 grams/liter of oxytetracycline hydrochloride as a preservative. The stock solution of oxytetracycline hydrochloride was prepared by using 24 grams per liter of distilled water and sterilizing the solution at 121° C. for 30 minutes. The bacterin preparation is now ready to be used.

Antigenic material prepared by the process set out in the foregoing description of the invention was evaluated in the following tests.

EXAMPLE 1

Separate batches of approximately 60 rainbow trout weighing about 3.2 g each were vaccinated by immersing each batch of fish for 1.5 minutes in the previously described bacterin which was diluted with water 1:2, 1:10, and 1:40. The final immersion ratio was 454 g of fish per liter of bacterin. Controls consisted of immersing a separate batch of fish in hatchery water for 1.5 minutes. All fish were subsequently held for 29 days at 12° C. for immunity to develop.

The fish from each group were then challenged with virulent *Y. ruckeri*. The challenge solution in each instance was a 24-hour culture grown in tryptic soy broth at 22° C. The culture was then diluted 20-fold with hatchery water as a challenge bath. The fish were placed into this challenge bath for about 1 hour at 15° C. The exact challenge level was $1 \times 10^8$ organisms per ml.

Following the exposure to challenge bacteria, the fish were held at 16° C. for 14 days. The cause of death was verified by reisolation of the organism from the kidney of dead fish on tryptic soy agar followed by standard techniques such as colony morphology, grain stain, and slide agglutination.

The results obtained from this immersion test are shown in Table 1 (ERM=Enteric Redmouth):

TABLE 1

| Cumulative Mortality of Rainbow Trout (3.2g) Challenged with Virulent *Y. ruckeri* (Hagerman strain) 29 Day Post Immunization | | | |
|---|---|---|---|
| Bacterin dilution | Number of fish | Death to ERM | % Mortality |
| unvaccinated control | 65 | 47 | 72 |
| unchallenged control | 40 | 0 | 0 |
| 1:2 | 63 | 10 | 16 |
| 1:10 | 63 | 16 | 24 |
| 1:40 | 66 | 15 | 23 |

The fish immunized with the ERM bacterin were significantly protected from a virulent challenge of *Y. ruckeri*. No significant difference was found between the bacterin dilutions. Thus efficacy was demonstrated with a single 1.5 minute immersion and such is an effective means of immunization.

EXAMPLE 2

In this example rainbow trout (2.2 g avg. wt.) were immunized using a 20 second immersion and three different bacterin preparations (prepared as described above) were compared using a 1:10 and 1:20 dilution. In addition, these same bacterins were administered by injecting 0.05 ml into each fish. There were about 150 fish in each test group. In each case the three bacterin preparations were standardized so that each resulted in an optical density of 0.5 (Bausch and Lomb Spectronic 20 at 525 nm) when diluted 1:5 with water. Further dilutions were made with water from these standardized preparations. Fish were held at 15° C. for 25 days when about 50 fish were removed for challenge. The challenge was exactly as described in Example 1 except that the challenge solution contained $3.3 \times 10^8$ organisms per ml. The results are shown in Table 2

TABLE 2

| | | Cumulative Mortality of Rainbow Trout (2.2g avg. wt.) Challenged with Virulent *Y. ruckeri*. 25 Days Post Immunization | | | | | | | | |
|---|---|---|---|---|---|---|---|---|---|---|
| Method of vaccination | Preparation number | 1:10 Bacterin* | | | 1:20 Bacterin** | | | Controls | | |
| | | n | loss | % | n | loss | % | n | loss | % |
| 20 sec. immersion | 104T | 50 | 10 | 20.0 | 49 | 12 | 24.5 | 24 | 21 | 87.5 |
| | 105T | 45 | 10 | 22.2 | 49 | 9 | 18.4 | 26 | 18 | 69.2 |

TABLE 2-continued

Cumulative Mortality of Rainbow Trout (2.2g avg. wt.) Challenged with Virulent *Y. ruckeri.* 25 Days Post Immunization

| Method of vaccination | Preparation number | 1:10 Bacterin* | | | 1:20 Bacterin** | | | Controls | | |
|---|---|---|---|---|---|---|---|---|---|---|
| | | n | loss | % | n | loss | % | n | loss | % |
| | 106T | 48 | 11 | 22.9 | 48 | 14 | 29.2 | 25 | 20 | 80.0 |
| Total | | 143 | 31 | 21.7 | 146 | 35 | 24.0 | 75 | 59 | 78.7 |
| injection | 104T | 46 | 0 | 0 | 45 | 0 | 0 | 24 | 16 | 66.7 |
| | 105T | 50 | 0 | 0 | 50 | 0 | 0 | 26 | 13 | 50.0 |
| | 106T | 49 | 0 | 0 | 46 | 4 | 8.7 | 23 | 13 | 56.5 |
| Total | | 145 | 0 | 0 | 141 | 4 | 2.8 | 73 | 42 | 57.5 |

*1:10 bacterin is one field dose
**1:20 bacterin is ½ field dose

Although the immersed fish were not as protected as the injected groups, there was a high degree of protection.

The average mortality was 78.7% in the control immersed group compared to an average of 21.7% in the 1:10 diluted bacterin and 24.0% in the 1:20 diluted groups. By comparison, the mortality was 0 and 2.8%, respectively, for the 1:10 and 1:20 bacterin preparations that were injected.

These same groups were held and again challenged at 76 days and 125 days post immunization to determine if the protection was transient. In this case, the 76 day and 125 day challenges consisted of $2.5 \times 10^8$ and $4.6 \times 10^8$ organisms per ml, respectively. The results are shown in Table 3.

It is apparent that there was no loss in immunity over the 125-day test period in any group and perhaps there was some increased protection in the 1:10 immersed group. It is concluded that the 20 second immersion is an effective method of immunizing fish against Enteric Redmouth.

TABLE 3

ERM Bacterin Duration Test Challenge Results

| Days Post-Vaccination | | Immersion | | Injection[1] | Control |
|---|---|---|---|---|---|
| | | 1:10 | 1:20 | | |
| 25 days | N | 143 | 146 | 238 | 75 |
| | ERM Loss | 31 | 35 | 4 | 59 |
| | % ERM Loss | 21.7 | 24.0 | 1.7 | 78.7 |
| 76 days | N | 23 | 52 | 51 | 47 |
| | ERM Loss | 3 | 12 | 0 | 29 |
| | % ERM Loss | 13.0 | 23.1 | 0 | 61.6 |
| 125 days | N | 60 | 61 | 60 | 59 |
| | ERM Loss | 7 | 15 | 1 | 35 |
| | % ERM Loss | 11.7 | 24.6 | 1.7 | 59.3 |

[1] 1:10 and 1:20 groups combined

EXAMPLE 3

In this example chinook salmon (1.8 g avg. wt.) were used and the value of a booster was evaluated. About 300 fish were vaccinated on day 1 using a 20 second immersion. On day 14 one-half (150) were revaccinated as before and another 150 fish were vaccinated. After holding the fish for 34 days at 10° C., each group was divided into three subgroups and each subgroup was challenged at a different challenge level. Challenges were conducted as described in Example 1. The results are shown in Table 4.

TABLE 4

Cumulative Mortality of Fall Chinook Vaccinated with ERM Bacterin to Evaluate Booster Effect

| Challenge level (organisms per ml) | | No Booster | | Booster Vaccinated Days 1 & 14 | Positive Control |
|---|---|---|---|---|---|
| | | Vaccinated Day 1 | Vaccinated Day 14 | | |
| $3.0 \times 10^8$ | N | 46 | 38 | 46 | 48 |
| | ERM Loss[a] | 2 | 5 | 2 | 22 |
| | % ERM Loss | 4.3 | 13.2 | 4.3 | 45.8 |
| $1.5 \times 10^8$ | N | 44 | 42 | 47 | 41 |
| | ERM Loss[a] | 4 | 4 | 0 | 21 |
| | % ERM Loss | 9.1 | 9.5 | 0 | 51.2 |
| $7.5 \times 10^8$ | N | 39 | 36 | 50 | 46 |
| | ERM Loss[a] | 3 | 1 | 1 | 20 |
| | % ERM Loss | 7.7 | 2.7 | 2.0 | 43.5 |

[a] ERM Loss = Those fish from which *Y. ruckeri* was recovered and attributed as the cause of death.

This example shows that chinook salmon can be effectively immunized using a 20 second immersion and that a booster given 14 days apart does not significantly increase protection. Furthermore, the protection is about the same when the fish are challenged at several challenge levels. In this test control mortality ranged between 43.5% and 51.2% mortality but immunized mortality in single immersions was 2.7 to 13.2% and in booster groups 0 to 4.3%.

EXAMPLE 4

The effect of temperature on the immune response in fish is well documented. However, the effect of water temperature using the immersion method is not well known. This example shows that rainbow trout (2.0 g avg. wt.) can be immunized with the ERM bacterin over a wide range of temperatures. Groups of 250 fish were vaccinated using the 20 second immersion method held at 10, 15 and 20° C. Subgroups of about 50 fish were removed 7, 14, 21, 28 and 35 days post-vaccination and challenged with virulent *Y. ruckeri* as described in Example 1. The results are shown in Table 5.

These results show that it takes about 21 days post-vaccination for fish to become protected. Furthermore, the onset of protection is delayed at 10° C. compared to 20° C. These results are not much different from that reported for other delivery techniques, and demonstrates that the 20 second immersion methods can successfully immunize fish under most hatchery conditions.

TABLE 5

Effect of Holding Temperature on Onset of Protection in Rainbow Trout Vaccinated with Enteric Redmouth Bacterin

| Days post-vaccination | | Temperature (Degrees C.) 10 | 15 | 20 | Positive Control | Challenge level (cfu/ml) |
|---|---|---|---|---|---|---|
| 7d | N[1] | 44 | 47 | 46 | 47 | |
| | ERM Loss | 13 | 7 | 6 | 38 | |
| | % | 29.5 | 14.9 | 13.0 | 80.9 | $1.7 \times 10^8$ |
| 14d | N | 59 | 64 | 40 | 58 | |
| | ERM Loss | 14 | 3 | 7 | 35 | |
| | % | 23.7 | 4.7 | 17.5 | 60.5 | $1.4 \times 10^8$ |
| 21d | N | 50 | 41 | 48 | 47 | |
| | ERM Loss | 4 | 5 | 3 | 37 | |
| | % | 8.0 | 12.2 | 6.3 | 78.8 | $6.5 \times 10^8$ |
| 28d | N | 59 | 55 | 56 | 58 | |
| | ERM Loss | 4 | 1 | 4 | 46 | |
| | % | 6.7 | 2.0 | 7.1 | 79.0 | $3.0 \times 10^8$ |
| 35d | N | 51 | 49 | 51 | 49 | |
| | ERM Loss | 2 | 1 | 2 | 27 | |
| | % | 3.9 | 2.0 | 3.9 | 55.1 | $2.6 \times 10^8$ |

[1] N = number of fish

EXAMPLE 5

The following recipe provides an approximate liter of Soybean Casein Digest Broth:

| Formula: | gr/liter |
|---|---|
| Pancreatic Digest of Casein | 17.0 |
| Papaic Digest of Soybean Meal | 3.0 |
| NaCl | 5.0 |
| $K_2HPO_4$ | 2.5 |
| Dextrose | 2.5 |
| Distilled $H_2O$ | Q.S. to liter |

Preparation

The components of the medium are purchased individually from commercial sources and combined or premixed powdered medium obtained from a commercial source. 1,000 ml of distilled water is added to the mixed components. The pH of the medium is then adjusted to $7.3 \pm 0.2$ using 5.0 NHd or 10.0 N. NaOH as needed.

Sterilization

The medium is sterilized by autoclaving for a minimum of 30 minutes at 121° C., 15 p.s.i.

Maximum Storage Temperature and Time

The sterilized medium is stored at 4° C. until used, and no longer than 4 weeks.

EXAMPLE 6

The following recipe provides an approximate liter of Soybean Casein Digest Agar:

| Formula: | gr/liter |
|---|---|
| Pancreatic Digest of Casein | 15.0 |
| Papaic Digest of Soybean Meal | 5.0 |
| NaCl | 5.0 |
| Agar | 15.0 |
| Distilled Water | 1,000 ml |

Preparation

The components of the medium are purchased individually from commercial sources and combined or premixed powdered medium obtained from a commercial source. 1,000 ml of distilled water is added to the mixed components. The pH of the medium is then adjusted to $7.3 \pm 0.2$ using 5.0 NHd or 10.0 N. NaOH as needed.

Sterilization

The medium is sterilized by autoclaving for a minimum of 30 minutes at 121° C., 15 p.s.i.

Maximum Storage Temperature and Time

The sterilized medium is stored at 4° C. until used, and no longer than 4 weeks.

EXAMPLE 7

The following recipe provides 4,000 ml of Mist Desiccans.

| Ingredients | Grams/Liter |
|---|---|
| Peptone | 5.0 |
| Beef Extract | 3.0 |
| Glucose | 30.0 |
| Distilled Water, q.s. ad 1,000 ml | |
| Sterile Horse Serum, q.s. ad 4,000 ml | |

The first four ingredients are combined and sterilized for example, by filtration through a $0.22\mu$ membrane filter. After sterilization, the sterile horse serum is added and the sterile medium dispensed into suitable sterile containers. The medium which is observed for evidence of contamination prior to use, is stored at 2° to 8° C. until used or for a period of no longer than 120 days.

From the foregoing description and examples, it is evident that the instant invention affords a method for preparing a vaccine for the immunization of fish against Enteric Redmouth which comprises:

(a) inoculating a liquid bacteriological culture supplying all metabolic requirements for the bacterium Y. ruckeri;

(b) incubating the inoculated culture medium at a temperature and for a period of time sufficient to produce substantial numbers of bacterial cells; and (c) inactivating the culture medium.

The foregoing test results also show that best protection against Enteric Redmouth is obtained with the instant vaccine comprising an immunologically effective amunt of the described bacterin component. The concentration of bacterin in the instant vaccine should be at least $10^4$ and, preferably, from about $10^5$ to about $10^9$, inactivated organisms per ml of vaccine. Higher concentrations are also suitable but deemed unnecessary with regard to efficacy of end product. The most preferred concentration of bacterin is from about $10^6$ to about $10^8$ organisms per ml. It should be understood that the bacterin described herein could also be used with other isolates or serotypes of Y. ruckeri.

As previously shown, the method of immunization comprises the simple immersion of fish in the vaccine for a period of time sufficient to confer immunity, generally at least 5 seconds and, preferably, from about 5 to about 120 seconds, although longer periods can be tolerated.

For field use purposes, the instant vaccine is preferably provided in the form of a concentrate which can be simply diluted, for example, with water or saline, to the desired effective concentration of bacterin. Accordingly, the instant invention contemplates the preparation as heretofore described of such concentrated vaccine for example which, upon suitable dilution, say 1:1 to about 1:20 (vaccine:diluent) will provide an immersion bath solution of at least $10^4$ of the inactivated organism per ml of bath.

The temperature of the immersion bath is not critical, the limitation being comfort of the fish. However, the onset of immunity may vary directly with the temperature. For example, at 10° C. it has been found that immunity is afforded in about 21 days whereas at 18° C., it is observed within 5 to 10 days.

It will be understood that the present invention is not limited to the immunization of fish named hereinabove, but includes other teleost fish, rainbow trout, chinook salmon, and the like.

Further to be understood is that the invention is not limited to the particular embodiment or methods described, but embraces all such modified forms as may come within the scope of the following claims.

What is claimed is:

1. A method for the immunization of fish weighing at least about one gram against Enteric Redmouth which consists essentially of the non-pressurized immersion without hyperosmotic treatment of the fish in a vaccine comprising an immunologically effective amount of the killed organism *Y. ruckeri* for a period of time sufficient to confer immunity to the fish.

2. A method for the immunization of fish weighing at least about one gram against Enteric Redmouth which consists essentially of the non-pressurized immersion without hyperosmotic treatment of the fish in a vaccine comprising an immunologically effective amount of the killed organism *Y. ruckeri* in a concentration of at least $10^4$ of said killed organism per ml of vaccine for at least 5 seconds.

3. The method of claim 2 wherein the concentration is from about $10^6$ to about $10^8$ of the organism per ml of vaccine.

4. The method of claim 2 wherein the immersion time is from about 5 to about 120 seconds.

* * * * *